United States Patent [19]

Ruoslahti et al.

[11] Patent Number: 5,547,936
[45] Date of Patent: *Aug. 20, 1996

[54] INHIBITION OF CELL MIGRATION WITH SYNTHETIC PEPTIDES

[75] Inventors: Erkki I. Ruoslahti, Rancho Santa Fe; Michael D. Pierschbacher; Kurt R. Gehlsen, both of San Diego, all of Calif.

[73] Assignee: La Jolla Cancer Research Foundation, La Jolla, Calif.

[*] Notice: The term of this patent shall not extend beyond the expiration date of Pat. No. 4,578,079.

[21] Appl. No.: 169,743

[22] Filed: Dec. 17, 1993

Related U.S. Application Data

[63] Continuation of Ser. No. 773,106, Oct. 8, 1991, abandoned, and a continuation-in-part of Ser. No. 902,742, Jun. 19, 1992, which is a continuation of Ser. No. 660,526, Feb. 25, 1991, abandoned, which is a continuation of Ser. No. 242,713, Sep. 9, 1988, Pat. No. 5,041,380, which is a continuation of Ser. No. 744,981, Jun. 17, 1985, Pat. No. 4,792,525, which is a division of Ser. No. 554,821, Nov. 22, 1993, Pat. No. 4,578,079, said Ser. No. 773,106, is a continuation of Ser. No. 683,585, Apr. 10, 1991, abandoned, which is a continuation of Ser. No. 166,530, Mar. 10, 1988, abandoned.

[51] Int. Cl.⁶ .......................... A61K 38/04; A61K 38/07; A61K 38/16
[52] U.S. Cl. ................. 514/12; 514/18; 514/17; 530/324; 530/300; 435/240.2; 435/7.23
[58] Field of Search .................. 435/7.21, 7.23, 435/240.2, 240.243, 240.241, 240.23; 530/300, 329, 330, 353, 356; 514/2, 12, 13, 14, 15, 16, 17, 18

[56] References Cited

U.S. PATENT DOCUMENTS

| | | | |
|---|---|---|---|
| 4,578,079 | 3/1986 | Ruoslahti et al. | 623/11 |
| 4,614,517 | 9/1986 | Ruoslahti et al. | 530/330 |
| 4,988,621 | 1/1991 | Ruoslahti et al. | 435/240.2 |

FOREIGN PATENT DOCUMENTS

| | | | |
|---|---|---|---|
| 0275748 | 7/1988 | European Pat. Off. | |

OTHER PUBLICATIONS

McCarthy et al. 1986. J. Cell. Biol. 102, 179–188.
*Chambers Science and Technolog Dictionary* (Walker et al., eds.) 1988. W. R. Chambers Ltd. and Cambridge Univ. Press. Cambridge, pp. 29, 284, 566, 863,78. (Supplied by appl. in Prelim. amendment).
Humphries et al. 1986. Science 233, 467–470.
Hendrix et al. 1985. Clin. Exp. Metastasis 3, 221–223.
Pierschbacher et al. 1984, Nature, 309, 30—33.
Goodman et al. 1985 Embo J. 4, 2769–2771.
Gehlsen et al. 1987, J. Cell Biol. 105(4 part 2) abstract 236, p. 44a.
Pierschbacher et al., Influence of Stereochemistry of the Sequence Arg–Gly–Asp–XAA on Binding Specificity in Cell Adhesion. J. Biol. Chem. 262(36):17294–17298 (1987).
Gehlsen et al., Inhibition of In Vitro Tumor Cell Invasion by Arg–Gly–Asp–Containing Synthetic Peptides. Chem. Abstracts. 108:391, Abstract No. 219712r (1988).
Gehlsen et al., Inhibition of In Vitro Tumor Cell Invasion by Arg–Gly–Asp–Containing Synthetic Peptides. J. Cell. Biol. 106(3):925–30 (1988).
Dedhar et al., "A Cell Surface Receptor Complex for Collagen Type I Recognizes the Arg–Gly–Asp Sequence" *J. Cell Biol.* 104:585–593 (1987).

*Primary Examiner*—Christopher S. F. Low
*Attorney, Agent, or Firm*—Campbell & Flores

[57] ABSTRACT

A method of inhibiting the invasion of cells, particularly malignant cells through an extracellular membrane by contacting the membrane-cell interface with synthetic Arg-Gly-Asp-containing peptides. In one embodiment, the invention provides peptides containing the amino acid sequence Arg-Gly-Asp-Thr, more specifically Gly-Arg-Gly-Asp-Thr-Pro, which inhibits the attachment of cells to type I collagen in addition to fibronectin and vitronectin, and a method of inhibiting the attachment of cells to type I collagen. The invention further provides an assay for quantitating the invasive quality of cells by determining the amount of such peptides necessary to prevent the cells from penetrating an extracellular membrane, such as an amniotic membrane, in vitro.

3 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Gly Arg Gly Glu Ser Pro
1               5

( 2 ) INFORMATION FOR SEQ ID NO:2:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:2:

Gly Arg Gly Asp Thr Pro
1               5

( 2 ) INFORMATION FOR SEQ ID NO:3:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:3:

Arg Gly Asp Thr
1

( 2 ) INFORMATION FOR SEQ ID NO:4:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:4:

Gly Arg Gly Asp Ser Pro
1               5

( 2 ) INFORMATION FOR SEQ ID NO:5:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:5:

Gly Arg Gly Asp Asn Pro
1               5

( 2 ) INFORMATION FOR SEQ ID NO:6:

( i ) SEQUENCE CHARACTERISTICS:
( A ) LENGTH: 10 amino acids
( B ) TYPE: amino acid ( D ) TOPOLOGY: circular ( i x ) FEATURE:
    ( A ) NAME/KEY: Modified-site
    ( B ) LOCATION: 2
    ( D ) OTHER INFORMATION: /note="X=Pen"

( x i ) SEQUENCE DESCRIPTION: SEQ ID NO:6:

Gly Xaa Gly Arg Gly Asp Ser Pro Cys Ala
1               5                   10

INHIBITION OF CELL MIGRATION WITH SYNTHETIC PEPTIDES

This application is a continuation of application Ser. No. 733,106, filed Oct. 8, 1991, now abandoned, which is a continuation of application Ser. No. 683,585, filed Apr. 10, 1991, now abandoned, which is a continuation of application Ser. No. 166,530, filed Mar. 10, 1988, now abandoned and a continuation-in-part of application Ser. No. 902,472, filed Jun. 19, 1992, now pending, which is a continuation of application Ser. No. 660,526, filed Feb. 25, 1991, now abandoned, which is a continuation of application Ser. No. 242,713, filed Sep. 9, 1988, now U.S. Pat. No. 5,041,380, which is a continuation of application Ser. No. 744,981, filed Jun. 17, 19985, now U.S. Pat. No. 4,792,525, which is a divisional of application Ser. No. 554,821, filed Nov. 22, 1983, now U.S. Pat. No. 4,578,079.

The present invention relates to synthetic cell adhesion peptides and, more specifically, to their use in inhibiting cell migration.

The interactions of cells with extracellular matrix components such as fibronectin, vitronectin and type I collagen have been shown to be mediated through a family of cell surface receptors that specifically recognize an arginine-glycine-aspartic acid (Arg-Gly-Asp or RGD) amino acid sequence within each protein. Such receptor-ligand interactions are critical to the orderly migration and differentiation of cells and tissues during development, and to the continued maintenance of normal cell to cell interactions. Synthetic peptides containing the Arg-Gly-Asp sequence are capable of competing with adhesion proteins for their receptors, thereby inhibiting cell attachment of both normal and tumor cells on substrates coated with the adhesion proteins.

Occasionally, normal cell adhesion interactions may become disrupted resulting in inappropriate and potentially deleterious migration of cells, such as occurs in metastasis.

The metastatic process is comprised of a complex series of events the details of which are largely unknown. For a tumor cell to be metastatic, it must be capable of attaching to the extracellular matrices that separate tissues and must penetrate such matrices. These matrices are composed of macromolecules that include fibronectin, laminin, collagens and proteoglycans. The interactions of cells with the extracellular matrix is mediated by cell surface receptors, including those which recognize and specifically bind to RGD containing sequences.

There thus exists a need for a composition capable of inhibiting the undesirable attachment to and/or penetration of extracellular matrices by cells. The present invention satisfies such a need and provides related advantages as well.

SUMMARY OF THE INVENTION

The present invention provides a method for inhibiting the invasion of cells, particularly malignant cells, through an extracellular membrane by contacting the membrane-cell interface with synthetic Arg-Gly-Asp-containing peptides. In one embodiment, the invention provides peptides containing the amino acid sequence Arg-Gly-Asp-Thr (SEQ. ID NO: 3), more specifically Gly-Arg-Gly-Asp-Thr-Pro (SEQ. ID NO: 2), which inhibits the attachment of cells to type I collagen in addition to fibronectin and vitronectin, and a method of inhibiting the attachment of cells to type I collagen. Preferably, such peptides are stabilized to prevent their breakdown in a cellular environment. Such stabilization may be accomplished by conjugating the peptides to polymers such as polymeric sugars. The invention further provides an assay for quantitating the invasive quality of cells by determining the amount of such peptides necessary to prevent the cells from penetrating an extracellular membrane, such as an amniotic membrane, in vitro.

DETAILED DESCRIPTION OF THE INVENTION

Figure 1A:
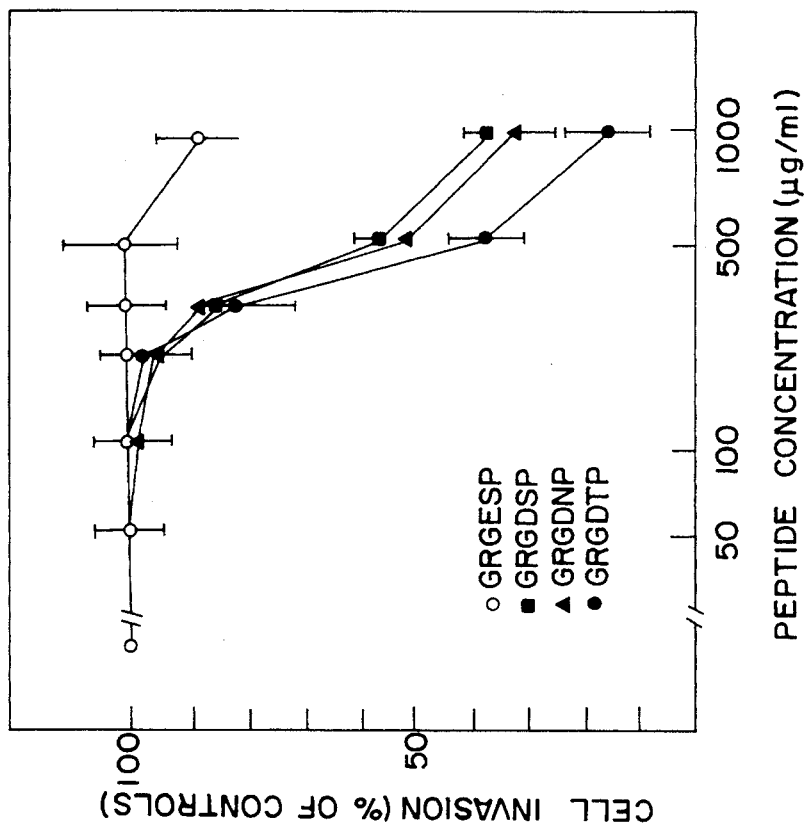
FIGS. 1A and 1B show the effect of Arg-Gly-Asp-containing peptides on tumor cell invasion, using the MICS invasion system. The numbers of cells that had accumulated in the lower chamber compartment at 72 hours were used to calculate invasion. The uninhibited control values were set at 100% with the data derived from nine observations for each point. The mean and standard deviation is shown as a percentage of tumor cell invasion relative to the controls.

The present invention relates to methods of inhibiting the invasion of cells through extracellular membranes by providing Arg-Gly-Asp-containing synthetic peptides. This inhibition is concentration dependent, non-toxic and correlates with both the ability of the peptides to interact with matrix adhesion receptors and with the invasive quality of the cells. Herein, all peptides are referred to by their standard three letter abbreviation, or one letter symbol, as detailed in, for example, U.S. Pat. No. 4,578,079, which is incorporated herein by reference.

For tumor cells to migrate through a membrane, such as an amniotic membrane, they must go through a series of steps. First, the cells have to attach to the basement membrane, a step which appears to be important in both in vitro as well as in in vivo invasion systems. Peptides containing the sequence Arg-Gly-Asp show only minimal inhibition of the attachment of tumor cells to the basement membrane and have no detaching effect after the cells have already attached to it. Next, the cells must penetrate into and through the stromal portion of the membrane, which in the amnion is about four-fifths the thickness of the membrane. While not wishing to be bound by this explanation, it is believed that the Arg-Gly-Asp containing peptides inhibit this step of the invasion process. In agreement with this belief is the fact that stromal extracellular matrix contains the adhesive proteins fibronectin and type I collagen, cell attachment to which is specifically inhibited by the particular Arg-Gly-Asp-containing peptides shown to have the greatest inhibitory effect.

The invention further provides specific Arg-Gly-Asp-containing peptides having particular efficacy in inhibiting membrane invasion by tumor cells. Such peptides include those having the amino acid sequences Arg-Gly-Asp-Thr (SEQ ID NO: 3), and, more particularly, the sequence Gly-Arg-Gly-Asp-Thr-Pro (SEQ ID NO: 2). It is contemplated that such peptides may or may not include various other amino acids, or other chemical moieties, on either the amino terminal or carboxy terminal side of these specific sequences, provided that such additional moieties do not interfere with the ability of the peptides to inhibit membrane invasion, and, moreover, provided that such peptides are not identical to naturally occurring peptides.

The length of the synthetic peptides utilized in the present invention is limited by their solubility. Over about thirty amino acid residues the solubility becomes so reduced that they are not feasibly utilized. Preferably, the peptides under about thirty amino acids in length, more preferably four to ten, or more preferably five to eight.

Preferably, these peptides are stabilized so that they will not be quickly broken down or otherwise eliminated in a cellular or in vivo environment. Such stabilization may be effected by conjugating the peptides to organic polymers, such as polymeric sugars, preferably dextran. The molecular weight of the polymer can be specifically chosen to provide for the desired longevity, the higher molecular weight correlating with a longer half life of the conjugate.

There is further provided an in vitro assay system for quantitatively determining the invasive quality, or "invasiveness index" of particular cells. The assay system includes two chambers, the "seeding chamber" and the "target chamber" separated by an extracellular membrane, such as an amniotic membrane. Both chambers contain growth medium appropriate for the maintenance of the cells utilized. Cells suspected of being malignant are placed in the seeding chamber for a time sufficient to permit them to attach to and penetrate the membrane. Thereafter, the growth medium from one or both of the chambers is collected and the presence of cells therein determined. The presence of cells in the target chamber indicates that the cells are capable of membrane invasion.

In order to quantitate the degree of invasiveness possessed by the cells, the described assay is repeated with increasing concentrations of Arg-Gly-Asp-containing, invasion-inhibiting peptides being added to the seeding chamber. Such peptides may be added contemporaneously with the addition of the cells to the chamber, or preferably, may be added at a time determined to correlate with the penetration of the cells into and through the stromal portion of the membrane. The concentration of peptide necessary to achieve a particular level of invasion inhibition correlates with the invasiveness of the cells, providing an "invasiveness index".

Arg-Gly-Asp-containing peptides, particularly those stabilized so as not to be rapidly broken down in the body, may be useful in counteracting the invasion of tumor cells through connective tissue matrices. When provided with appropriate physiologically acceptable excipients and in amounts sufficient to inhibit such invasion, such Arg-Gly-Asp-containing peptides may be therapeutically useful in preventing the metastasis of tumor cells.

The following examples are intended to more clearly illustrate aspects of the invention, but are not intended to limit the scope thereof.

EXAMPLE I

Preparation of Synthetic Peptides

Peptides were synthesized using an automated peptide synthesizer (Model 430A; Applied Biosystems, Foster City, Calif.), using the instructions provided by the manufacturer, and purified by reverse phase HPLC on a Biogel TSK SP-5-PW cation exchange column (Bio-Rad Laboratories, Richmond, Calif.).

Where appropriate, cyclization was accomplished as follows. 611 mg of the synthesized peptide were dissolved in 4 L of water that had been previously boiled and allowed to cool. Immediately prior to addition of the peptide, nitrogen was bubbled through the water for 45 minutes. After the peptide was dissolved, a solution of 0.1 ug/mL of potassium ferrous cyanide $K_3[Fe(CN)_6]$ in water was added dropwise to the stirred peptide solution until the yellow color persisted for 5 minutes (approximately 5 ml). The pH of the solution was held at 7.0 throughout this procedure by addition of $NH_4OH$. The solution was allowed to stand for 20 hours under low vacuum and then lyophilized. Excess $K_3[Fe(CN)_6]$ was removed by passing the cyclized material over a Sephadex G-15 column (1.8×120 cm). The peptide was purified by reverse phase HPLC using a Waters Bondapak™ $C_{18}$ column (3×30 cm; 10 um packing) (Waters Assoc., Milford, Mass.). The peptide was loaded on the column in buffer A (20 mM ammonium acetate at pH 7.5) and eluted with a gradient of buffer B consisting of 60% acetonitrile and 40% buffer A. The major peak obtained from the $C_{18}$ column constituted 90% of recovered peptide and was deduced to be a monomeric cyclic peptide because it was retained on the column for the length of time predicted for that sequence and because the uncyclized material and the multimeric forms were well separated from the main peak.

The following peptides were synthesized for testing:

Gly-Arg-Gly-Glu-Ser-Pro (SEQ. ID NO: 1)
Gly-Arg-Gly-Asp-Ser-Pro (SEQ. ID NO: 4)
Gly-Arg-Gly-Asp-Asn-Pro (SEQ. ID NO: 5)
Gly-Arg-Gly-Asp-Thr-Pro (SEQ. ID NO: 2)
Gly-Arg-Gly-Asp-D-Ser-Pro (SEQ. ID NO: 7)

(SEQ ID NO: 6)
Gly—Pen—Gly—Arg—Gly—Asp—Ser—Pro—Cys—Ala
      |_____|

Gly—D—Arg—Gly—Asp—Ser—Pro    (SEQ ID NO: 8)

EXAMPLE II

Cell Invasion Assays

Invasiveness of tumor cells was determined using a modification of the Membrane Invasion Culture System (MICS) as described in Hendrix et al (1985) Clin. Exp. Metastasis 3:221–223, which is incorporated herein by reference. The cell lines used included two human melanoma cell lines designated A375P and A375M, the derivation and metastatic properties of which have been described in Kozlowski et al., (1984) Journal of The National Cancer Institute, 72:913, and a human glioblastoma cell line (RuGli) described in Goodman and Newgreen (1985) EMBO 4: 2769. Noninvasive fibroblasts were used as control cells. All of the cells were cultured in DME (Gibco, Chagrin Falls, OH) supplemented with 10% heat inactivated fetal bovine serum (Tissue Culture Biologicals, Tulare, Calif.) and 0.1% gentamicin (Gibco). Cells were removed from culture dishes using 2 mM EDTA in PBS devoid of $Ca^{++}$ and $Mg^{++}$ for all assays. Cells ($5×10^4$ to $1×10^5$) were radiolabelled with 0.25 uCi/ml $^{14}C$-thymidine (New England Nuclear (Boston, Mass.) for 48 hours in DMEM containing 2% fetal bovine serum and then seeded into the upper compartment of the MICS chambers prepared as follows.

Fresh human placentas were obtained at birth, and in each case the amnion was obtained from near the region of the umbilical cord. After several rinses in sterile PBS, Fungizone/penicillin/streptomycin (Irvine Scientific, Irvine, Calif.) and PBS again, the amnion was trimmed to fit specially designed MICS chambers as depicted in Gehlsen and Hendrix, (1987) Pigment Cell 1:16–21, FIG. 1. The amnion was aseptically interposed between the top and bottom plates of the MICS apparatus, with the epithelial surface facing the top plate. The fastening screw was tightened and the extra membranous material trimmed away with a scapel. Before fitting the membrane in the chamber, the bottom wells (the "target wells") were filled with sterile DMEM (Gibco) containing 10% fetal bovine serum. The amniotic epithelium was removed by treatment with freshly prepared 0.25 M ammonium hydroxide ($NH_4OH$) for 5 minutes at room temperature followed by extensive washing in PBS, which left a denuded basement membrane with an underlying collagenods stroma. In this manner, the interaction of cells with an extracellular matrix could be studied without the interference of host cells.

The labelled cells were delivered into each upper, or "seeding" chamber in serum-containing DMEM at a final concentration of $1.0 \times 10^5$/ml and placed in a humidified incubator at 37° C. with 5% $CO_2$ and 95% air atmosphere. All membranes were carefully examined for leakiness prior to cell seeding by allowing the denuded basement membrane surface to incubate for 1 hour with density marker beads (Pharmacia Fine Chemicals, Piscataway, N.J.) with a buoyant density of 1.049 g/ml in a percoll gradient containing 0.25 M sucrose. If the colored beads, which were measured to be the same density as the cells from each cell line, were detected in the bottom wells of MICS, those portions of the membranes were not used.

The number of cells able to successfully invade the basement membrane and underlying collagenous stroma was determined by removing the media in the lower wells (1.1 ml) after each 24 hour increment and 72 hours via the side ports in the MICS chambers without disruption of the ongoing experiment. After each lower well was sampled, fresh media was replenished in the lower wells. In this manner, tumor cell invasion could by assessed repeatedly in the same experiment over various time intervals. The $^{14}C$-thymidine radio-labelled cells in all the lower well samples were pelleted and then placed in scintillation vials. In all experiments, the collected $^{14}C$-labelled cells were then lysed with 0.5 ml of 1 N NaOH. Aliquots of 100 ul glacial acetic acid were added to each vial to prevent chemiluminescence, and 10 ml of ACS scintillation cocktail (Amersham Corporation, Arlington Heights, Ill.) was added prior to radiolabel determination using a scintillation counter (Beckman Instruments).

For the peptide studies, peptides were added after a preattachment incubation period at 37° C. in a 7% $CO_2$-air atmosphere and at 24 hour intervals thereafter, at which time medium in both the upper and lower compartments of the chambers was replaced with fresh, peptide-containing medium. At specific time intervals after the addition of peptides, medium from the upper and lower chambers was removed, the membranes were washed with fresh medium and the medium and wash fractions were centrifuged and the number of cells in the cell pellets was determined by counting the cell-associated radioactivity by liquid scintillation. The total number of cells that had passed through the membrane was derived by adding the lower chamber value to those from the previous samplings. In several experiments, unlabelled cells were used and the cells were counted in a hemocytometer. In addition, the number of cells that could partially but not completely invade the amnion was determined. The amnion was treated in tissue solubilizer (Amersham Corporation, Arlington Heights, Ill.) before counting cell-associated radioactivity.

Figure 1B:
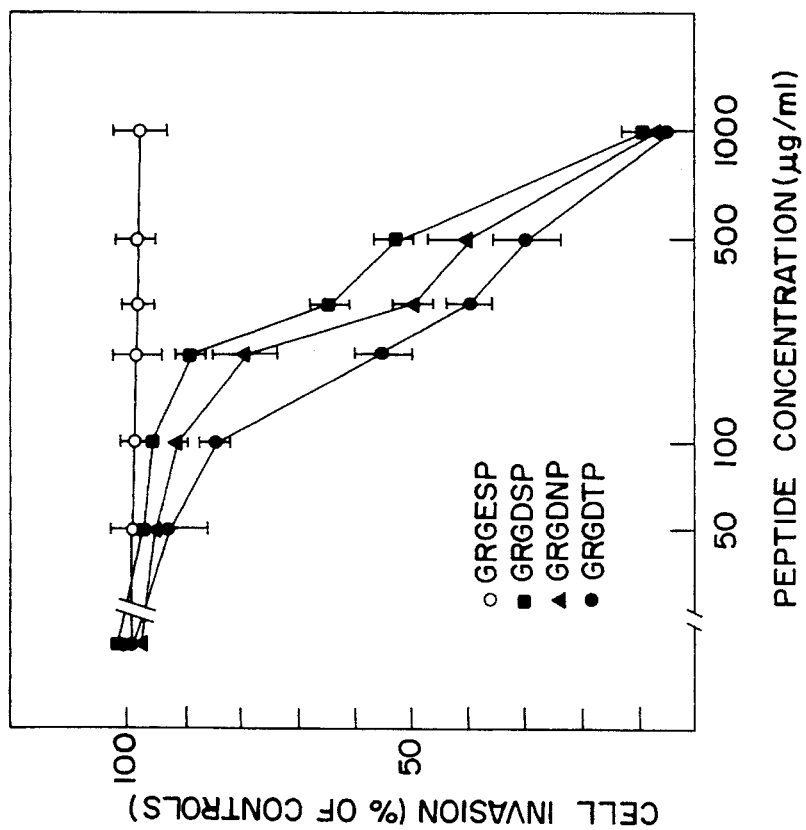

Seven to nine percent of the A375M cells, 3 to 5% of the A375P cells and 7 to 12% of the RuGli cells seeded onto the membranes traversed the amnion in 72 hours. A marked decrease in the invasion was seen in the presence of Arg-Gly-Asp-containing peptides with all three cell lines. This inhibition of invasion was apparent at all time points analyzed, but it was greatest at 72 hours. For this reason, this time point was used in the subsequent experiments. Results from such an experiment in which several Arg-Gly-Asp-containing peptides and a control peptide were tested with the A375M and RuGli cells are shown in FIG. 1. The data show that each of the Arg-Gly-Asp-containing peptides inhibited invasion, whereas the control peptide in which the aspartic acid has been substituted with glutamic acid rendering it inactive in cell attachment assays was without effect. A hexapeptide with a D-alanine in the place of the second glycine was also inactive.

The results shown in FIG. 1 indicate that Arg-Gly-Asp-containing adhesion proteins and their receptors play a role in tumor cell invasion. Differing degrees of inhibition were associated with specific sequences. The Gly-Arg-Gly-Asp-Thr-Pro (SEQ. ID NO: 2) peptide which, unlike Gly-Arg-Asp-Ser-Pro (SEQ. ID NO: 4) and Gly-Arg-Gly-Asp-Asn-Pro (SEQ. ID NO: 5), inhibits the attachment of cells to type I collagen as well as to fibronectin and vitronectin was consistently the most active of those tested in the MICS system, suggesting that type I collagen plays some role in the invasion process. Gly-Arg-Gly-Asp-D-Ser-Pro (SEQ. ID NO: 4), which inhibits attachment to fibronectin but not to vitronectin was as active as Gly-Arg-Gly-Asp-Ser-Pro (SEQ. ID NO: 4), while the cyclic peptide, which inhibits attachment predominantly to vitronectin was an inefficient inhibitor of invasion.

EXAMPLE III

Visualization of Cell Location During Invasion

Figure 2A:
FIGS. 2A and 2B show a visualization of invading tumor cells within the amniotic membrane. The cells were labelled with a fluorescent dye and allowed to invade the amniotic membrane for 72 hours in the presence of either Gly-Arg-Gly-Asp-Glu-Ser-Pro (SEQ. ID NO: 1) (GRGESP photograph A) or Gly-Arg-Gly-Asp-Thr-Pro (SEQ. ID NO: 2) (GRGDTP photograph B). The visualization of cell location during the invasion period was then determined by fluorescent microscopic examination of the sectioned amniotic membrane. Basement membrane surface (upper arrow) and the lower stromal surface (lower arrow) of the amniotic membrane are shown.
Figure 2B:
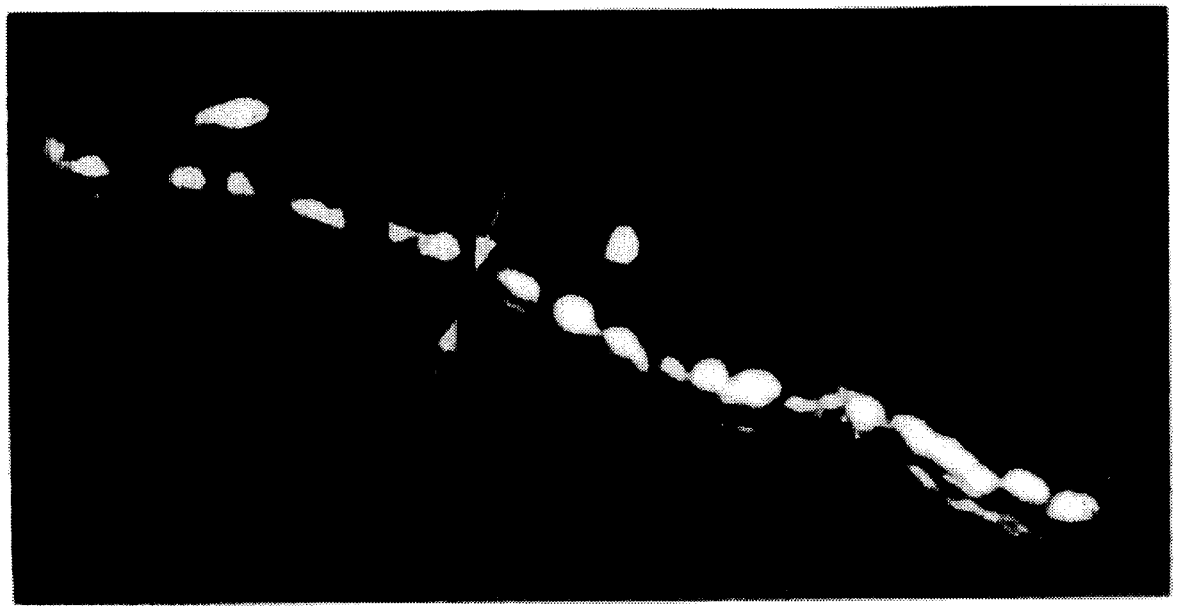

To visualize the invading cells in the amniotic membrane, fluorescently labelled cells were seeded onto amniotic membranes in MICS chambers as detailed in Example II. The labelled cells invaded as efficiently as unlabelled cells and the Gly-Arg-Gly-Asp-Thr-Pro (SEQ ID NO: 2) peptide inhibited this invasion. Cross sections of the amniotic membranes were examined by fluorescent light microscopy to locate the cells. In experiments performed with a control peptide, Gly-Arg-Gly-Glu-Ser-Pro (SEQ. ID NO: 1), cells at various stages of migration throughout the amnion were observed (FIG. 2A), whereas examination of over 100 sections from experiments with the Gly-Arg-Gly-Asp-Thr-Pro (SEQ. ID NO: 2) peptide revealed no cells within the amnion stroma. In this case, the cells were located at the basement membrane surface or directly beneath the basement membrane (FIG. 2B).

Although the invention has been described with reference to the presently-preferred embodiments, it should be understood that various modifications can be made by those skilled in the art without departing from the invention. Accordingly, the invention is limited only by the following claims.

---

We claim:

1. A method of inhibiting tumor cell invasion through an extracellular matrix by contacting said tumor cell and said extracellular matrix with a synthetic peptide containing the amino acid sequence $Xaa_1$-Arg-Gly-Asp-$Xaa_2$-$Xaa_3$, wherein $Xaa_1$ is one or more amino acids or H, $Xaa_2$ is an amino acid, and $Xaa_3$ is one or more amino acids or OH, neither $Xaa_1$, $Xaa_2$, nor $Xaa_3$ interfere with the ability of said synthetic peptide to inhibit said tumor cell invasion, said synthetic peptide is soluble and less than about thirty amino acids long and said synthetic peptide inhibits said tumor cell invasion.

2. The method of claim 1 wherein said synthetic peptide is Gly-Arg-Gly-Asp-Thr-Pro.

3. A method of inhibiting tumor cell invasion through an extracellular matrix by contacting said tumor cell and said extracellular matrix with a synthetic peptide containing the amino acid sequence Arg-Gly-Asp, wherein said synthetic peptide is soluble and inhibits said tumor cell invasion.

* * * * *

UNITED STATES PATENT AND TRADEMARK OFFICE
CERTIFICATE OF CORRECTION

PATENT NO. : 5,547,936
DATED : August 20, 1996
INVENTOR(S) : Ruoslahti, et. al.

It is certified that error appears in the above-identified patent and that said Letters Patent is hereby corrected as shown below:

In column 1, line 15, please delete "19985" and replace therefor with --1985--.

In column 4, line 64, please delete "placentas" and replace therefor with --placentae--.

In column 5, line 15, please delete "collagenods" and replace therefor with --collagenous--.

In column 5, line 38, please delete "by" and replace therefor with --be--.

In column 6, lines 25 and 26, please delete "Gly-Arg-Asp-Ser-Pro (SEQ. ID NO: 4)" and replace therefor with --Gly-Arg-Gly-Asp-Ser-Pro (SEQ. ID NO: 4)--.

UNITED STATES PATENT AND TRADEMARK OFFICE
CERTIFICATE OF CORRECTION

PATENT NO. : 5,547,936
DATED : August 20, 1996
INVENTOR(S) : Ruoslahti, et. al.

It is certified that error appears in the above-identified patent and that said Letters Patent is hereby corrected as shown below:

In column 6, line 32, please delete "NO:4)" and replace therefor with -- NO: 7)--.

Signed and Sealed this

Sixth Day of April, 1999

Attest:

Attesting Officer

Q. TODD DICKINSON

Acting Commissioner of Patents and Trademarks